(12) United States Patent
Fanselow et al.

(10) Patent No.: US 10,436,729 B2
(45) Date of Patent: Oct. 8, 2019

(54) METHOD FOR MANUFACTURING A CONDUCTIVITY SENSOR

(71) Applicant: Endress+Hauser Conducta GmbH+Co. KG, Gerlingen (DE)

(72) Inventors: Christian Fanselow, Geringswalde (DE); André Pfeifer, Schkopau (DE); Thomas Nagel, Dresden (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 318 days.

(21) Appl. No.: 15/375,294

(22) Filed: Dec. 12, 2016

(65) Prior Publication Data

US 2017/0167996 A1 Jun. 15, 2017

(30) Foreign Application Priority Data

Dec. 15, 2015 (DE) .................... 10 2015 121 857

(51) Int. Cl.
*G01N 27/07* (2006.01)
*G01R 3/00* (2006.01)
*G01R 31/28* (2006.01)

(52) U.S. Cl.
CPC ............. *G01N 27/07* (2013.01); *G01R 3/00* (2013.01); *G01R 31/2829* (2013.01)

(58) Field of Classification Search
CPC .................................. G01R 3/00; G01N 27/07
See application file for complete search history.

(56) References Cited

U.S. PATENT DOCUMENTS

| 2008/0171181 A1* | 7/2008 | Zaderej | H05K 1/0373 |
| | | | 428/209 |
| 2010/0321046 A1* | 12/2010 | Randall | G01N 27/07 |
| | | | 324/696 |

FOREIGN PATENT DOCUMENTS

| CN | 101147056 A | 3/2008 |
| CN | 102498366 A | 6/2012 |
| DE | 102 17 698 A1 | 6/2003 |
| DE | 103 17 879 A1 | 11/2004 |
| DE | 103 55 921 A1 | 6/2005 |
| DE | 10 2005 053 973 A1 | 5/2007 |

OTHER PUBLICATIONS

Search Report for German Patent Application No. 10 2015 121 857.7, German Patent Office, dated Mar. 11, 2016, 9 pp.
Holhjem, et al., Electrode Compositions for Laser Patterned Conductometric Sensors, 2014 Electronics System-Integration Conference, 6 pp. (Abstract Provided).

\* cited by examiner

*Primary Examiner* — Seahvosh Nikmanesh
(74) *Attorney, Agent, or Firm* — Christopher R. Powers; PatServe

(57) ABSTRACT

The present disclosure relates to a method for manufacturing a conductivity sensor, including a conductive conductivity sensor, including method steps of producing a thermoplastic sensor body of a plastic, which is doped at least partially with a laser activatable, metal compound as an additive, radiating the sensor body at doped locations by means of a laser, so that conductive metal nuclei form from the metal compound, immersing the sensor body in a metal bath, until at least one conductive trace forms on the region having the metal nuclei, where the at least one conductive trace serves as an electrode of the conductivity sensor.

10 Claims, 2 Drawing Sheets

METHOD FOR MANUFACTURING A CONDUCTIVITY SENSOR

CROSS-REFERENCE TO RELATED APPLICATION

The present application is related to and claims the priority benefit of German Patent Application No. 10 2015 121 857.7, filed on Dec. 15, 2015, the entire contents of which are incorporated herein by reference.

TECHNICAL FIELD

The present disclosure relates to a method for manufacturing a sensor, in particular a conductivity sensor.

BACKGROUND

Known from the state of the art are conductive conductivity sensors comprising at least two electrodes, which are immersed for measuring in the measured medium. For determining the electrolytic conductivity of the measured medium, the resistance or conductance of the electrode measuring path in the measured medium is determined. In the case of a known cell constant, the conductivity of the measured medium can then be ascertained.

Shown in DE 10 2006 024 905 A1 is an electrode arrangement of a conductive conductivity sensor, in the case of which an inner and an outer electrode are separated from one another and insulated relative to one another by a shaped seal and a seal support body. The shaped seal serves to avoid penetration of measured medium into an annular gap between the electrodes.

Such an electrode arrangement with additional seals is constructively relatively complex. This is the case especially for conductivity sensors destined for application in foods technology or in the pharmaceutical industry. High hygienic requirements are placed on such sensors. For example, the probes of such sensors, to the extent that they come in contact with the measured medium, are not permitted to have any difficultly accessible gaps, in order that a cleaning and/or sterilizing of the total probe surface contacting the measured medium is possible. Conventional seals or a shaped seal according to DE 10 2006 024 905 A1 can, indeed, basically fulfill these requirements, but they involve complex construction with correspondingly increased effort for their assembly.

SUMMARY

An object of the present disclosure is to provide a method for manufacturing a conductivity sensor and a corresponding conductivity sensor, which fulfills high hygienic requirements and, in spite of this, is simple to manufacture.

The object is achieved by the subject matter of the present disclosure, including a method for manufacturing a conductivity sensor, including a conductive conductivity sensor, comprising method steps of producing a thermoplastic sensor body of a plastic, which is doped at least partially with a laser activatable, metal compound as an additive, structuring the doped sensor body by means of a laser, so that conductive metal nuclei form from the metal compound, immersing the sensor body in a metal plating bath, until at least one conductive trace forms on the sensor body, wherein at least one of the conductive traces serves as an electrode of the conductivity sensor.

The structuring of the doped sensor body by means of a laser produces an MID (Molded Interconnect Device). MIDs are injection molded, plastic components with specially applied metal conductive traces to serve as circuit supports for electronic or mechatronic assemblies.

Integration of conductive traces and metallized contact feedthroughs in the sensor body leads to a miniaturizing of the conductivity sensor. Furthermore, the number of components and mounting steps are reduced.

Laser direct structuring (LDS) utilizes a thermoplastic plastic doped with a non-conductive, laser activatable, metal compound as an additive. A laser beam writes the paths of the subsequently applied conductive traces on the plastic. Where the laser beam strikes the plastic, the surface of the plastic matrix is decomposed into volatile, cracking, or splitting products, such that the surface is slightly removed. At the same time, metal nuclei are split off from the additive. These metal nuclei lie finely distributed in the micro roughened surface, and, as metal particles, form the nuclei for the subsequent metallizing. Upon immersion into an electroless copper bath, sharply defined conductive trace layers form on the lasered surface portions. Following this, layers of copper, nickel and a gold finish can be sequentially applied.

The subject matter of the present disclosure further includes a conductivity sensor produced using a method of the present disclosure, wherein the at least one conductive trace is arranged on an area of the sensor body facing the measured medium.

In a further development, the sensor body includes at least one plug contact for producing an electrical contact to the at least one conductive trace.

In a variant, the sensor body includes at least one metallized contact feedthrough, which electrically connects the at least one conductive trace with the at least one plug contact.

In at least one embodiment, the sensor body includes a recess with a temperature sensor for measuring the temperature of the measured medium.

In a further embodiment, at least one of the conductive traces is injection mold coated for insulation.

BRIEF DESCRIPTION OF THE DRAWINGS

The present disclosure will now be explained in greater detail based on the appended drawing, the figures of which show as follows.

DETAILED DESCRIPTION

Figure 1:
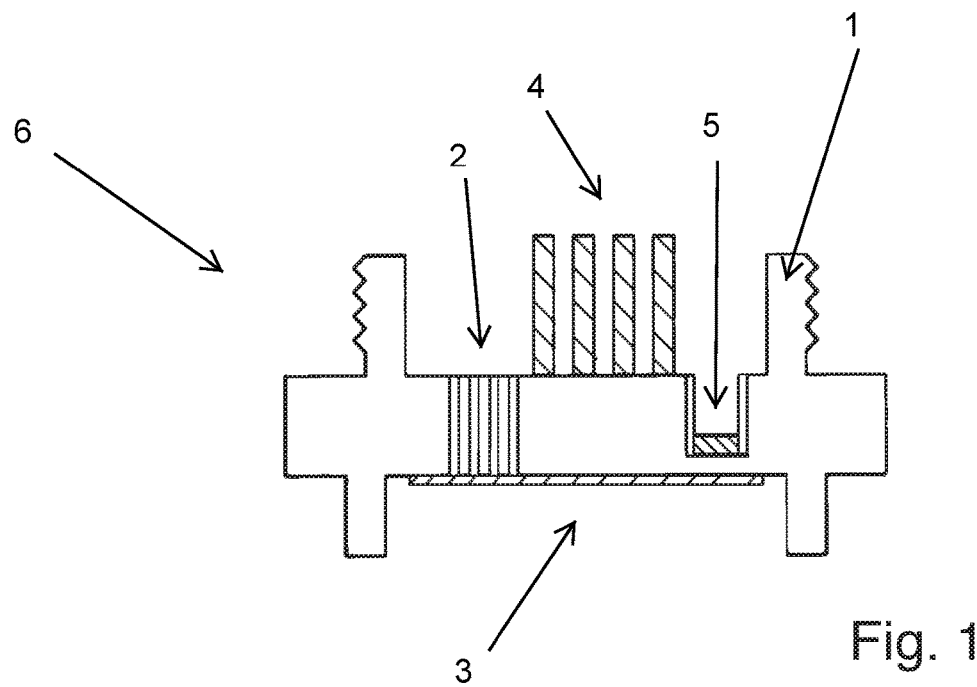
FIG. 1 shows a longitudinal section of a conductivity sensor according to the present disclosure.

FIG. 1 shows a longitudinal section of a conductive conductivity sensor 6 produced according to a method of the present disclosure. Conductivity sensor 6 includes a sensor body 1 having conductive traces 3, wherein the conductive traces 3 are arranged on an area of the sensor body 1 facing the measured medium. The sensor body 1 includes, furthermore, plug contacts 4 for establishing electrical contact with an electronics unit (not shown) capable of supplying the conductive traces 3 with electrical voltage, in order to determine the conductivity of the medium. Metallized contact feedthroughs 2 provide electrical connection between the conductive traces 3 and the plug contacts 4. Furthermore, the sensor body 1 includes a recess equipped with a temperature sensor 5 for measuring the temperature of the measured medium.

The sensor body 1 is produced by injection molding of a thermoplastic plastic doped with a laser activatable, metal compound. The resulting sensor body 1 is structured by means of a laser using the LDS method. The structuring produces conductive metal nuclei from the metal compound. The sensor body is then immersed in a metal plating bath to form the conductive traces 3 on the sensor body 1, wherein the conductive traces 3 serve as electrodes of the conductivity sensor 6.

After the above manufacturing steps, the sensor body 1 is injection mold coated with plastic, in order to make the conductivity sensor 6 even more hygienic and so to assure optimum process compatibility.

Figure 2:
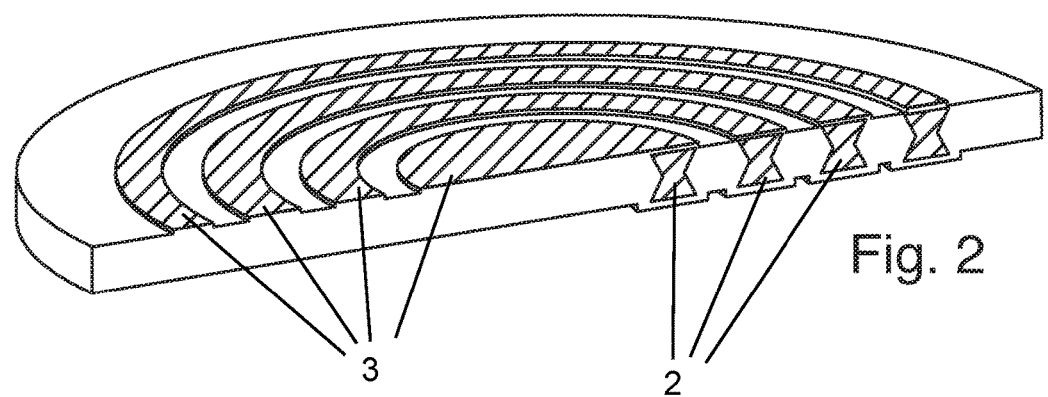
FIG. 2 shows a perspective view of a longitudinal section of a conductivity sensor according to the present disclosure.

FIG. 2 shows a perspective view of a longitudinal section of a conductivity sensor 6 of FIG. 1 from a side of the sensor body 1 facing the measured medium. The conductive traces 3 are circularly and annularly embodied.

The manufacturing process for a conductive conductivity sensor 6 makes unnecessary the applying of conductive traces and metallized contact feedthroughs in some alternate procedure producing an additional layer on the contact feedthroughs 2. The LDS method means that no additional layers are applied on the sensor body 1. Therefore, no gaps result, which are difficult to clean and to sterilize. For this reason, the conductivity sensor manufactured by means of the LDS method is more hygienic than conventional conductivity sensors from the state of the art.

Figure 3:
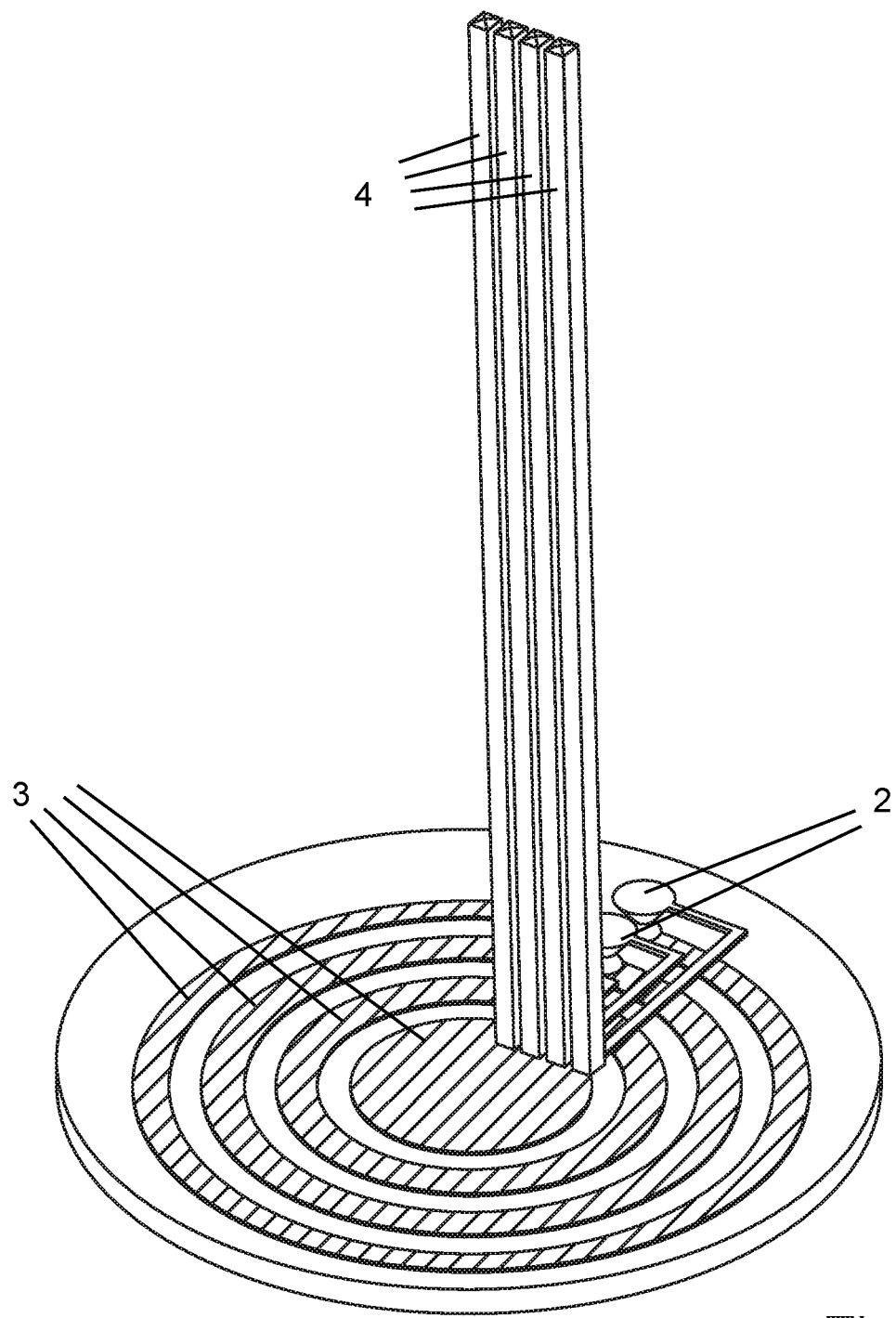
FIG. 3 shows a perspective view of the interior of a conductivity sensor according to the present disclosure.

FIG. 3 shows a plan view onto the interior of a conductivity sensor of FIG. 1.

The invention claimed is:

1. A method for manufacturing a conductivity sensor comprising method steps as follows:
   forming a thermoplastic sensor body of a plastic, the plastic at least partially doped with a laser activatable, metal compound as an additive;
   structuring the sensor body using a laser to form at least one trace path on a first side of the sensor body and at least one feedthrough aperture through the sensor body, such that conductive metal nuclei form from the metal compound on surfaces of the sensor body defining the at least one trace path and the at least one feedthrough aperture; and
   immersing the sensor body in a metal plating bath until, from the conductive metal nuclei, at least one conductive trace forms on the at least one trace path and until at least one contact feedthrough forms in the at least one feedthrough aperture, wherein the at least one conductive trace is formed in electrical communication with the at least one contact feedthrough, wherein at least one of the conductive traces serves as an electrode of the conductivity sensor.

2. A conductivity sensor produced by the method of claim 1, wherein the at least one conductive trace is arranged on an area of the sensor body facing a measured medium.

3. The conductivity sensor of claim 2, wherein the sensor body includes at least one plug contact in electrical contact with the at least one conductive trace via the contact feedthrough.

4. The conductivity sensor of claim 2, wherein the sensor body includes a recess in which a temperature sensor adapted for measuring the temperature of the measured medium is disposed.

5. The conductivity sensor of claim 2, wherein a portion of the sensor body includes a coating of plastic injection molded thereon to assure process compatibility.

6. The conductivity sensor of claim 2, wherein the conductivity sensor is a conductive conductivity sensor.

7. The method of claim 1, wherein the structuring of the sensor body to form the at least one feedthrough aperture includes directing the laser toward the first side of the sensor body upon which the at least one trace path is formed and from an opposing second side.

8. The method of claim 7, wherein the structuring of the sensor body to form the at least one feedthrough aperture further includes translating the laser relative to the sensor body such that the at least one feedthrough aperture has a cross-sectional area that varies from the first side to the second side.

9. The method of claim 8, wherein the at least one feedthrough aperture has a substantially double frusto-conical shape.

10. The conductivity sensor of claim 4, wherein the recess includes at least one contact configured to enable a connection to the temperature sensor, thereby enabling a temperature signal to be communicated from the temperature sensor, wherein the at least one contact is formed by structuring the sensor body using the laser to form at least one contact area and by immersing the sensor body in a metal plating bath until the at least one contact forms on the at least one contact area.

* * * * *